United States Patent [19]

Jensen

[11] 4,388,135
[45] Jun. 14, 1983

[54] METHOD OF MANUFACTURING OSTOMY POUCHES

[75] Inventor: Ole R. Jensen, River Vale, N.J.

[73] Assignee: E. R. Squibb & Sons, Inc., Princeton, N.J.

[21] Appl. No.: 286,495

[22] Filed: Jul. 24, 1981

[30] Foreign Application Priority Data

Aug. 1, 1980 [DK] Denmark .......................... 3328/80

[51] Int. Cl.³ ........................ B32B 31/18; B32B 31/20
[52] U.S. Cl. .................................. 156/250; 604/332;
156/256; 156/272.2; 156/289; 156/513;
156/516; 156/537
[58] Field of Search ............... 156/261, 270, 289, 513,
156/272.2, 514, 516, 522, 537, 250, 256;
128/275, 283, 286; 53/416, 419, 455, 456

[56] References Cited

U.S. PATENT DOCUMENTS

| | | | |
|---|---|---|---|
| 2,418,392 | 4/1947 | Bender | 53/455 |
| 3,302,647 | 2/1967 | Marsan | 128/283 |
| 3,351,061 | 11/1967 | Nolan | 128/283 |
| 3,352,737 | 11/1967 | Jordan | 156/514 |
| 3,479,802 | 11/1969 | Fesco | 156/324 |
| 3,618,606 | 11/1971 | Brown et al. | 128/283 |
| 3,646,936 | 3/1972 | Marsan | 128/283 |
| 3,988,195 | 10/1976 | Henderson | 156/514 |
| 4,213,458 | 7/1980 | Nolan et al. | 128/283 |

*Primary Examiner*—Caleb Weston
*Attorney, Agent, or Firm*—Lawrence S. Levinson; Stephen B. Davis

[57] ABSTRACT

Ostomy pouches are manufactured by partially contour welding two pouch walls one of which has a stoma aperture over an area extending from the top edge of the pouch past the region of the weld seam around the aperture. A separator member is inserted into the partially welded pouch and an adhesive label is then welded or bonded to the pouch wall around the aperture. The separator member is withdrawn and the contour welding is completed to form the completed pouch.

4 Claims, 4 Drawing Figures

METHOD OF MANUFACTURING OSTOMY POUCHES

BACKGROUND OF THE INVENTION

Ostomy pouches are known in a series of different shapes and sizes adapted according to their purpose. However, it is a common feature that they ordinarily consist of two pouch walls welded together along their contour. One of the walls has an aperture which receives material discharged from the stoma. An adhesive label or faceplate is affixed to the pouch wall around the stomal aperture by welding or adhesion. The adhesive label permits the detachable fastening of the pouch on the user's body around stoma.

In the production of such ostomy pouches, the starting material used is generally two webs of weldable plastic sheet material that are advanced stepwise through an apparatus with three stations. The first station has a punching tool to produce the apertures in one of the webs, the adhesive label being welded onto said web around the apertures at the second station, and the two webs being subsequently brought together and united along a line corresponding to the wanted contour of the pouch by means of an annular welding electrode at the third station. The finished pouches may simultaneously be separated from the remaining sheet material.

As the contour welding operation cannot be carried out through the adhesive label it is a primary condition in this technique of production that the label be positioned entirely within the contour of the pouch. In many cases, this is completely acceptable. However, in other cases, it means that for production reasons the pouch must be made bigger than otherwise necessary or that the distance from the aperture to the top of the pouch must be lengthened. The use of a pouch having such increased dimensions can result in the upper part of the pouch pulling outwardly from the user's body as a consequence of the increase in weight when the pouch fills.

SUMMARY OF THE INVENTION

This invention is directed to a method of manufacturing ostomy pouches in which the adhesive label or faceplate can extend past part of or even past the whole pouch contour. The particular feature of this method consists in that the two pouch walls in a first step are partially contour welded together namely over an area extending from the top edge of the pouch past the region of the weld seam around the aperture. The adhesive label or faceplate is subsequently applied by welding while using a separator member introduced into the partially finished pouch. The separator functions as a base for the pouch wall to which the label is being welded. The contour welding operation is subsequently completed in a second step after withdrawal of the separator member.

This invention is also directed to the apparatus employed in performing the method and to the resulting pouch obtained by virtue of this new method.

BRIEF DESCRIPTION OF THE DRAWINGS

The method according to the invention is illustrated by the accompanying drawings, in which.

DETAILED DESCRIPTION OF THE INVENTION

Figure 1:
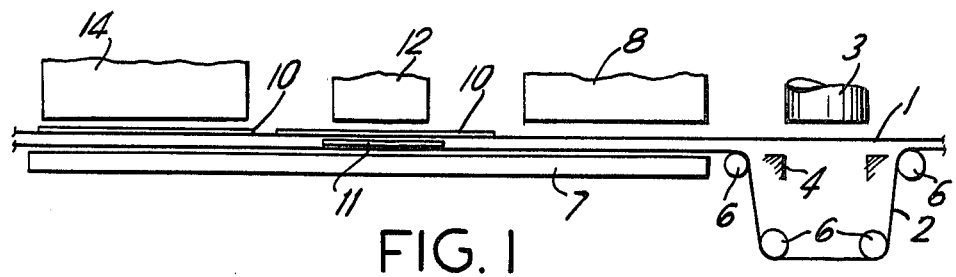
FIGS. 1 and 2 are schematic side elevational and plan views, respectively, showing the manufacturing of an ostomy pouch with its contour only partially overlapped by the adhesive label of the pouch.

An object of this invention is to provide a process of manufacture which allows the adhesive label or faceplate to extend past part of or even past the whole pouch contour. In other words, the adhesive label no longer determines the minimum size of the pouch nor the minimum distance from the aperture to the pouch edge. This invention permits the manufacture, for example, of extremely small ostomy pouches that can be safely placed at the stoma, and which, if desired, may serve only as a through-flow collector connected by a hose to a larger collection pouch. The larger collecting pouch could then be fastened to a place on the user's body such as around the leg where it will not hamper physical activity.

More particularly, this invention relates to a method of manufacturing ostomy pouches having two pouch walls welded together along their contour, one of the two walls being provided with an aperture and an adhesive label or faceplate welded or bonded to the pouch wall around said aperture which supports the pouch on the user's body. The particular feature of this method consists in that the two pouch walls in a first step are partially contour welded together namely over an area extending from one edge of the pouch past the region of the weld seam around the aperture. The adhesive label or faceplate is subsequently applied by welding or bonding while using a separator member introduced into the partially finished pouch. The separator functions as a base for the pouch wall to which the label is being welded. The contour welding aperture is subsequently completed in a second step after withdrawal of the separator member.

While the contour welding operations employed previously where effected in one step at the completion of the manufacturing process, the same operation according to the present invention is divided into two steps. One step is carried out prior and the other subsequent to the attachment of the adhesive label. The first step comprises welding the portion of the pouch contour that is inaccessible to be welded after the adhesive label has been applied and leaves a remaining area through which the separator member is introduced. The separator member is necessary to prevent the two pouch walls from being welded together around the aperture while the label is being welded or bonded to the aperture wall. When the separator member is afterwards withdrawn, the second step of the contour welding operation can be effected, thereby completing the pouch by closing the said remaining area. This permits the size and shape of the pouch to be freely chosen without regard to the size of the label or faceplate.

When the adhesive label covers only a portion of the pouch wall to which it is affixed, the first contour welding step can be adjusted so that the first weld extends a distance below the area that the pouch has in common with the adhesive label. The label when welded or bonded in place will not impede the second contour welding step which completes the pouch contour. However, when the pouch contour is completely within the contour of the adhesive label, the method is characterized in that the area for the first contour welding operation extends only a short distance past the region of the weld seam which affixes the label around the aperture. The portion of the adhesive label which extends beyond this region is temporarily lifted clear of the pouch wall as the second step of the contour welding is performed.

Figure 2:
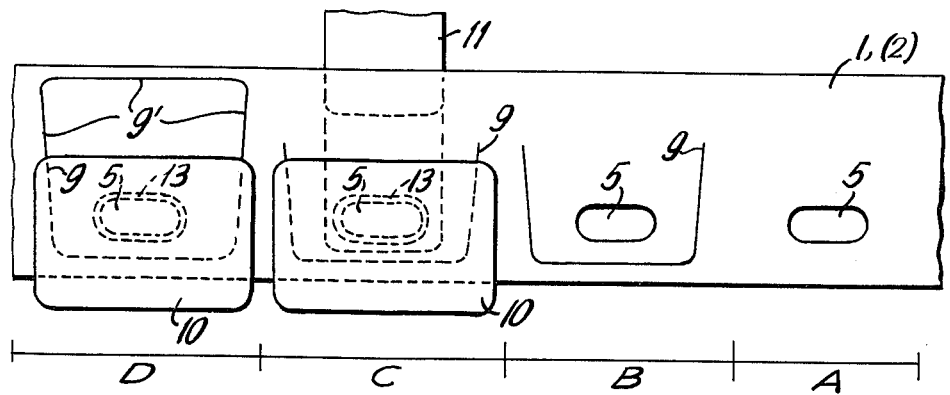

As shown in FIGS. 1 and 2, two superposed webs 1 and 2 of weldable plastic sheet material are passed stepwise through four stations A, B, C and D as shown in FIG. 2. Station A comprises a punch 3 and a corresponding matrix 4 to produce an aperture 5 in the uppermost web 1, and guide rollers 6 to guide the lowermost web 2 free of the punch tool 3, 4.

At stations B, C and D the two webs run forward across a table or base 7 at the same speed, a welding electrode 8 adapted to effect the above mentioned first step of the contour welding of the pouch walls being positioned above the right hand end of said table or base, namely in station B. The welded seam produced is indicated by 9 in FIG. 2.

In station C, an adhesive label 10 is placed on the top side of the uppermost web 1 in such a position that a prestamped aperture in the label coincides with the aperture 5 in the web or sheet material. At the same time, a separator member in the form of a flat tongue 11 is pushed into the pocket limited by the welded seam 9, and the adhesive label 10 is connected with the sheet 1 by means of an electrode 12 forming a seam 13 following the edge of the aperture 5.

After withdrawal of the tongue 11 from the pocket, the sheets 1 and 2 which are united through the welded seam 9, together with the adhesive label 10 solely fixed on the sheet 1, are advanced into station D where the ostomy pouch is completed. Electrode 14 in station D produces the supplemental weld seam 9' which together with weld seam 9 forms a completed or closed contour weld. As shown in FIG. 2, the supplementary or complementary portion 9' of said contour welding is outside the area of pouch wall 1 covered by label 10.

Figure 3:
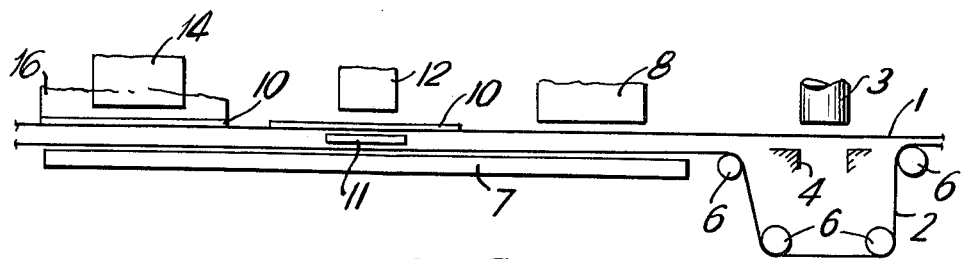
FIGS. 3 and 4 are similar views of the manufacturing of an ostomy pouch with its contour entirely inside the contour of the label.
Figure 4:
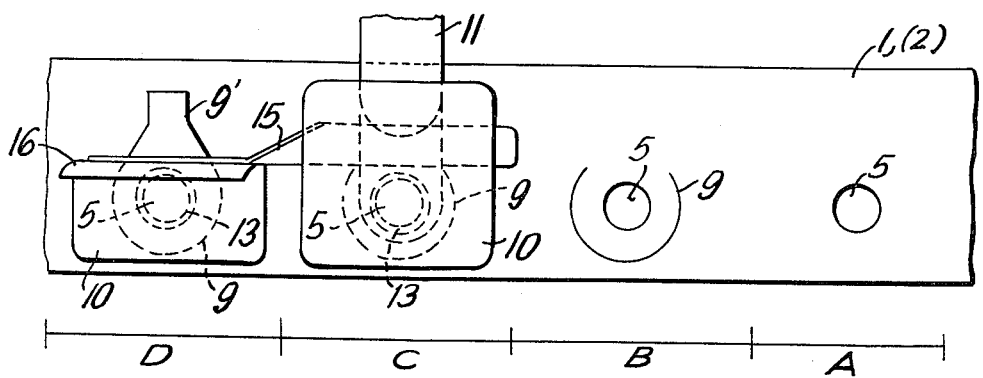

In FIGS. 3 and 4 the same reference numerals as in FIGS. 1 and 2 are used for analogous items. The most important difference is that the pouch contour 9, 9' as shown in FIGS. 3 and 4 is entirely placed within the contour of the adhesive label 10 so that said label when plane would impede electrode 14 from completing supplemental weld 9'. For this reason, a stationary guide 15 (shown in FIG. 4) is provided at stations C and D, to temperarily lift the portion of the adhesive label 10 overlying the first-step-welding 9 clear of the sheet, see the upright flap 16 in station D, thus providing a free working area for the electrode 14 to produce supplemental weld 9'.

It should be appreciated that the step of punching or cutting apperture 5 in the top web 1 could be performed after the first step of the contour welding. Thus, in the first station a partial contour weld seam 9 would be produced. The sheets would advance to a second station where the tongue 11 would be inserted, aperture 5 would be cut or punched in the top sheet 1 and the adhesive label 10 would be welded to the top sheet 1 by means of electrode 12 forming seam 13. After withdrawal of tongue 11, the sheets would be advanced to a third station where the contour weld 9' is made by electrode 14 so as to complete the pouch. Of course, if necessary, label 10 could be lifted as shown in FIGS. 3 and 4 so as not to interfere with electrode 14.

The adhesive label or faceplate 10 is a film of material capable of being welded or bonded by heat or R.F. energy to the pouch wall material and having a layer of pressure sensitive adhesive that supports the pouch on the body.

It should also be appreciated that aperture 5 need not be complete opening through the pouch wall. A tool could be employed which merely perforates or weakens the pouch wall along the circumference 5. The ostomate would then remove that portion of the pouch wall prior to using the pouch.

What is claimed is:

1. A method of manufacturing ostomy pouches having an adhesive label or faceplate that attaches the pouch to the body comprising;
   (a) advancing two superposed webs of weldable plastics sheet material and producing an aperture only in the uppermost web;
   (b) welding said two webs to form a partial pouch contour said partial contour extending from the top edge of the pouch past the area of said aperture in said uppermost web;
   (c) inserting a separator member into the partially contour welded pouch to function as a base for said uppermost pouch wall;
   (d) welding or bonding an adhesive label or faceplate to said supported uppermost pouch wall around said aperture;
   (e) removing said separator member; and
   (f) completing the contour welding of said pouch walls so as to form a completed pouch of desired configuration.

2. The method of claim 1 wherein said pouch contour is completely within the contour of said adhesive label characterized in that said first contour welding step (b) is adjusted so that the weld extends only a short distance past the region of the weld seam which affixes said adhesive label and said label which extends beyond this region is temporarily lifted clear of said pouch wall as said second contour welding step (e) is performed.

3. A method of manufacturing ostomy pouches having an adhesive label or faceplate that attaches the pouch to the body comprising
   (a) advancing two superposed webs of weldable plastics sheet material;
   (b) welding said two webs to form a partial pouch contour said partial contour extending from the top edge of the pouch past the region to which the adhesive label is affixed;
   (c) inserting a separator member into the partially contour welded pouch to function as a base for the uppermost pouch wall;
   (d) producing an aperture in said supported uppermost pouch wall, said aperture being within the area of said partial contour weld;
   (e) welding or bonding an adhesive label or faceplate to said supported uppermost pouch wall around said aperture;
   (f) removing said separator member; and
   (g) completing the contour welding of said pouch walls so as to form a completed pouch of desired configuration.

4. The method of claim 3 wherein said pouch contour is completely within the contour of said adhesive label characterized in that the portion of said label which extends beyond the region of the initial partial contour weld is temporarily lifted clear of said pouch wall as said second contour welding step (g) is performed.

* * * * *